(12) United States Patent
Takagi et al.

(10) Patent No.: US 8,936,613 B2
(45) Date of Patent: Jan. 20, 2015

(54) MEDICAL DEVICE

(71) Applicant: Terumo Kabushiki Kaisha, Shibuya-ku (JP)

(72) Inventors: Toshiaki Takagi, Ashigarakami-gun (JP); Yousuke Ootani, Ashigarakami-gun (JP); Yusuke Sekine, Ashigarakami-gun (JP); Ryuusuke Takashige, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/848,913

(22) Filed: Mar. 22, 2013

(65) Prior Publication Data
US 2013/0237952 A1 Sep. 12, 2013

Related U.S. Application Data

(63) Continuation of application No. PCT/JP2011/068519, filed on Aug. 15, 2011.

(30) Foreign Application Priority Data

Sep. 27, 2010 (JP) ................................ 2010-215400

(51) Int. Cl.
*A61M 29/00* (2006.01)
*A61M 37/00* (2006.01)
(Continued)

(52) U.S. Cl.
CPC .......... *A61M 37/00* (2013.01); *A61B 17/12113* (2013.01); *A61B 17/12136* (2013.01);
(Continued)

(58) Field of Classification Search
CPC ..................... A61M 37/00; A61M 2025/1054; A61B 2017/00287; A61B 2017/00292
USPC ............... 604/103, 103.01, 103.02, 171, 907; 606/191–195, 198
See application file for complete search history.

(56) References Cited

U.S. PATENT DOCUMENTS 4,327,734 A * 5/1982 White, Jr. ........................ 606/195
4,441,495 A * 4/1984 Hicswa .......................... 606/195
(Continued)

FOREIGN PATENT DOCUMENTS

GB 1 530 565 A 11/1978
JP 53-26490 A 3/1978
(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued by the International Patent Office on Apr. 25, 2013, in the corresponding International Patent Application No. PCT/JP2011/068519. (6 pages).

(Continued)

*Primary Examiner* — Nicholas Lucchesi
*Assistant Examiner* — Gerald Landry, II
(74) *Attorney, Agent, or Firm* — Buchanan Ingersoll & Rooney PC

(57) ABSTRACT

A medical device is configured to position a bag member filled with a therapeutic substance in a prescribed region of the brain. The use of this medical device involves, with a sheath inserted in the brain region, filling a therapeutic substance into a bag member through an infusion tube, followed by retracting the sheath relative to the infusion tube until the bag member protrudes forward beyond the distal end of the sheath. After this, the bag member is put indwelling in the brain region by moving an operating member relative to the infusion tube to detach the bag member from the distal end of the infusion tube.

20 Claims, 6 Drawing Sheets

(51) Int. Cl.
*A61B 17/12* (2006.01)
*A61B 17/00* (2006.01)
*A61M 25/10* (2013.01)

(52) U.S. Cl.
CPC .............. *A61B2017/00287* (2013.01); *A61B 2017/00292* (2013.01); *A61B 2017/00893* (2013.01); *A61M 2025/1054* (2013.01)
USPC ........................................ 606/195; 604/103.02

(56) References Cited

U.S. PATENT DOCUMENTS

| | | | | |
|---|---|---|---|---|
| 4,545,367 A | * | 10/1985 | Tucci | 128/898 |
| 5,304,123 A | * | 4/1994 | Atala et al. | 604/514 |
| 5,411,475 A | | 5/1995 | Atala et al. | |
| 6,293,960 B1 | * | 9/2001 | Ken | 606/195 |
| 6,391,040 B1 | * | 5/2002 | Christoudias | 606/162 |
| 2003/0014036 A1 | | 1/2003 | Varner et al. | |
| 2003/0023262 A1 | | 1/2003 | Welch | |
| 2007/0265600 A1 | | 11/2007 | Barlow et al. | |
| 2008/0312715 A1 | * | 12/2008 | Asirvatham et al. | 607/45 |
| 2010/0262159 A1 | * | 10/2010 | McGuckin, Jr. | 606/110 |

FOREIGN PATENT DOCUMENTS

| | | |
|---|---|---|
| JP | 7-502426 A | 3/1995 |
| JP | 2000-279523 A | 10/2000 |
| JP | 2004-535257 A | 11/2004 |
| JP | 2005-500097 A | 1/2005 |
| WO | WO 2007/080940 A1 | 7/2007 |

OTHER PUBLICATIONS

International Search Report (PCT/ISA/210) issued on Sep. 20, 2011, by the Japanese Patent Office as the International Searching Authority for International Application No. PCT/JP2011/068519.

* cited by examiner

MEDICAL DEVICE

CROSS REFERENCES TO RELATED APPLICATIONS

The present application is a continuation application of International Application No. PCT/JP2011/068519 filed on Aug. 15, 2011, and claims priority to Japanese Patent Application No. 2010-215400 filed on Sep. 27, 2010, the entire content of both of which is incorporated herein by reference.

TECHNICAL FIELD

The present invention generally relates to a medical device, more particularly to a medical device by which a bag member filled with a therapeutic substance can be put indwelling (indwelled) in a predetermined brain region for treatment in the brain region.

BACKGROUND DISCUSSION

Conventionally, therapeutic treatment of a brain region has been performed by the so-called craniotomy, in which the cranial bones covering an outer peripheral portion of the brain are incised over a large extent. The craniotomy imposes a heavy burden on the patient, and recovery after the operation takes a long period of time. In view of this, there is a keen demand for a process for performing a brain region treatment without needing large craniotomy.

As means for administering a therapeutic substance such as medicinal liquids, neurotrophic factors, information transmission substances, genes and cells into a diseased part in the brain region, a method of inserting a medical device such as catheter into the brain region is contemplated.

For maintaining the efficacy of a therapeutic substance over a long period of time, on the other hand, slow or sustained release of the therapeutic substance to the diseased part is desired. In order to administer a therapeutic substance through a catheter inserted in a brain region over a long period of time, it is necessary to keep the catheter in the inserted state in the cranial bone for a rather long period of time. This imposes a significant influence on the patient, and is unfavorable from the viewpoint of sanitary control.

If a bag member or the like from which a therapeutic substance is released slowly or sustainedly can be indwelled at a predetermined position in a brain region, it would be possible to perform an effective treatment while alleviating the burden on the patient.

Japanese Application Publication No. 2004-535257 proposes a catheterization apparatus in which the distal end of the apparatus is provided with an implant device capable of being released into an internal body cavity of a patient.

The use of this catheterization apparatus ensures that an implant device filled with a therapeutic substance or the like can be indwelled in a patient's body.

On the other hand, in a brain region, the internal pressure is raised by the so-called brain pressure. When the implant device as described in Japanese Application Publication No. 2004-535257 is placed outside the catheter, therefore, the implant device may be compressed under the pressure from the brain tissues, during the period until the catheter is inserted to the diseased part. This may lead to such a problem as flow-out of the therapeutic substance contained in the implant device. Consequently, it becomes impossible to administer a sufficient amount of the therapeutic substance to the predetermined diseased part.

In recent years, there is a trend toward the use of capsules which envelope a therapeutic substance. This trend is from the viewpoint of handleability and sustained release in the body. If a catheter is inserted into a brain region in the condition where capsules are contained in the implant part as described in Japanese Application Publication No. 2004-535257, friction and collisions between the capsules would be generated during movement of the catheter, resulting in breakage of the capsules. Consequently, the therapeutic substance would flow out before the arrival of the catheter at the diseased part, and it would be impossible to administer a sufficient amount of the therapeutic substance to the predetermined diseased part.

SUMMARY

According to one aspect, a medical device comprises: a sheath possessing an open distal end; an infusion tube positioned inside the sheath and movable in an advancing and retracting manner relative to the sheath, with the infusion tube possessing an interior which opens at a distal end of the infusion tube; and a porous bag member including an opening which opens into an interior of the bag member, with the porous bag member being detachably positioned at the distal end of the infusion tube, and with the interior of the porous bag member communicating with the interior of the infusion tube, the bag member being positioned in the sheath. The medical device also includes closing means disposed at the opening of the bag member for closing the opening of the bag member by elastic force when the bag member is detached from the distal end of the infusion tube, and an operating member positioned in the sheath and movable in an advancing and retracting manner relative to the infusion tube to detach the bag member from the distal end of the infusion tube by moving the closing means forward relative to the infusion tube. The bag member is configured to be indwelled in a brain region by a process comprising: inserting the sheath into the brain region, filling the bag member with a therapeutic substance by way of the infusion tube, and retracting the sheath relative to the infusion tube until the bag member protrudes forward from the distal end of the sheath, with the inserting, filling and retracting being performed in any order; and thereafter moving the operating member relative to the infusion tube to detach the bag member from the distal end of the infusion tube.

The medical device disclosed here is configured so that a bag member filled with a therapeutic substance can be put indwelling at a desired position in a brain region.

The closing means is preferably composed of a pair of plate-shaped elastic members opposed to each other, and when the bag member is held on the distal end of the infusion tube, the pair of plate-shaped elastic members are elastically deformed so as to be spaced from each other and the infusion tube is inserted between the plate-shaped elastic members, whereas when the bag member is detached from the distal end of the infusion tube, the plate-shaped elastic members are joined to or urged towards each other so that the opening of the bag member is automatically closed.

The closing means can be composed of a ring-shaped elastic member, and when the bag member is held on the distal end of the infusion tube, the ring-shaped elastic member is elastically deformed so as to be enlarged in diameter and the infusion tube is inserted in the ring, whereas when the bag member is detached from the distal end of the infusion tube, the ring-shaped elastic member is reduced in diameter so that the opening of the bag member is automatically closed.

The closing means can also be composed of a cover member provided with a slit-shaped cut, with the cover member disposed at the opening of the bag member, and when the bag member is held on a distal end of the infusion tube, the cover member is elastically deformed to enlarge the cut of the cover member and the infusion tube is inserted in the cut, whereas when the bag member is detached from the distal end of the infusion tube, the cut is closed so that the opening of the bag member is automatically closed.

The medical device can also include an inner tube member in the inside of which the infusion tube is disposed, wherein the inner tube member acts as the operating member.

A configuration may also be adopted in which: the inside of the bag member is provided with a first engaging part; the infusion tube is provided with a second engaging part for disengageable engagement with the first engaging part, the second engaging part extending from a distal portion of the infusion tube; and when the bag member is held on the distal end of the infusion tube, the first engaging part and the second engaging part engage with each other to restrain the bag member from being positionally deviated relative to the infusion tube, whereas when the bag member is detached from the distal end of the infusion tube, the first engaging part and the second engaging part are disengaged from each other.

According to another aspect, a method for delivering a therapeutic substance to a brain region comprises: moving an infusion tube toward the brain region to position a bag member, which is detachably mounted at a distal end of the infusion tube, at the brain region, wherein the bag member possesses an open end which opens into an interior of the bag member, wherein the infusion tube is positioned in the opening while a portion of the bag member surrounds the distal end of the infusion tube, and wherein the infusion tube is movably positioned inside an inner tube member so that the inner tube member is movable relative to the infusion tube and the bag member. The method also includes moving the inner tube member in an advancing direction relative to the infusion tube and the bag member to push the bag member off the distal end of the infusion tube and position the bag member at the brain region, automatically closing the open end of the bag member when the bag member is pushed off the distal end of the infusion tube; and delivering a therapeutic substance in the bag member to the brain region.

The inside of the bag member can be filled with the therapeutic substance in a state in which it is surrounded by the sheath, and the bag member can be indwelled at a desired position in a brain region.

BRIEF DESCRIPTION OF DRAWINGS

FIGS. 3A and 3B illustrate the configuration of the distal portion of the medical device according to the first embodiment 1, wherein FIG. 3A is a perspective view showing a bag member held on a distal portion of an infusion tube, and FIG. 3B is a perspective view showing the bag member detached from the distal portion of the infusion tube.

FIGS. 4A-4D illustrate a manner of use of the medical device shown in FIG. 1, wherein FIG. 4A is a partial cross-sectional view of a brain region in which the medical device is inserted, FIG. 4B is a partial cross-sectional view of the brain region when the bag member protrudes from a distal end of a sheath, FIG. 4C is a partial cross-sectional view of the brain region when an inner tube member makes contact with a plate-shaped elastic member, and FIG. 4D is a partial cross-sectional view of the brain region when the bag member is detached from the distal portion of the infusion tube.

FIGS. 6A and 6B illustrate the configuration of a distal portion of a medical device according to a second embodiment, wherein FIG. 6A is a perspective view of a bag member held on a distal portion of an infusion tube, and FIG. 6B is a perspective view of the bag member detached from the distal portion of the infusion tube.

FIGS. 7A and 7B illustrate the configuration of a distal portion of a medical device according to a third embodiment, wherein FIG. 7A is a perspective view of a bag member held on a distal portion of an infusion tube, and FIG. 7B is a perspective view of the bag member detached from the distal portion of the infusion tube.

FIGS. 9A and 9B illustrate the configuration of a distal portion of a medical device according to a fifth embodiment, wherein FIG. 9A is a perspective view of a bag member held on a distal portion of an infusion tube, and FIG. 9B is a perspective view of the bag member detached from the distal portion of the infusion tube.

FIGS. 12A and 12B illustrate a distal portion of a medical device according to a modification of the fifth embodiment, wherein FIG. 12A is a side cross-sectional view of a bag member held on a distal portion of an infusion tube, and FIG. 12B is a side cross-sectional view of the bag member detached from the distal portion of the infusion tube.

DETAILED DESCRIPTION

Set forth below, with reference to the accompanying drawing figures, is a description of embodiments of a medical device representing examples of the medical device disclosed here.

Figure 1:
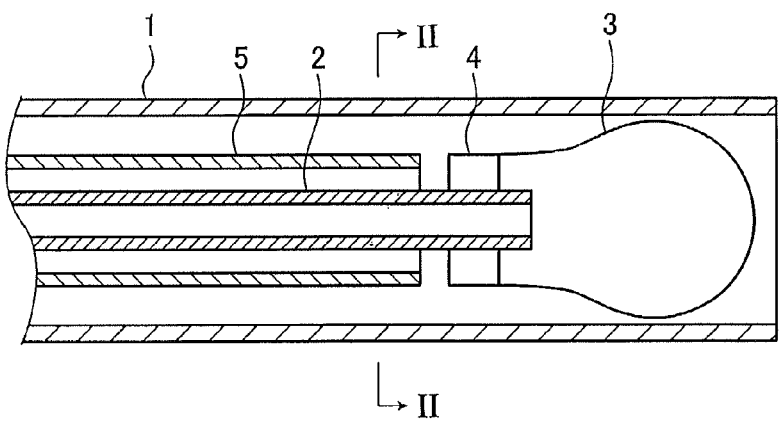
FIG. 1 is a longitudinal cross-sectional view of a distal portion of a medical device according to a first embodiment representing an example of the medical device disclosed here.

FIG. 1 illustrates the configuration of a distal portion of a medical device according to one embodiment. The medical device has a sheath 1 opened at its distal end, and an infusion tube 2 is inserted in the sheath 1 so as to be capable of being advanced and retracted. That is, the infusion tube 2 is positioned in the sheath 1 for advancing and retracting movement relative to the sheath Furthermore, a bag member 3 having an opening is detachably held on a distal portion of the infusion tube 2, and the bag member 3 (the inside of the bag member 3) and the infusion tube 2 (the inside of the infusion tube 2) communicate with each other through the opening of the bag member 3.

The infusion tube 2 functions to fill a therapeutic substance into the bag member 3 through the inside of the infusion tube 2. In addition, with the infusion tube 2 advanced and retracted relative to the sheath 1, the bag member 3 is also advanced and retracted in the sheath 1 together with the infusion tube 2. In other words, the infusion tube 2 functions also as operating means for advancing and retracting the bag member 3 relative to the sheath 1.

The cross-sectional shape of the infusion tube 2 is not limited to a specific shape, and may be an ellipse or a polygon. An optimum shape is appropriately selected through combination with an opening means 4 which will be described later.

Figure 2:
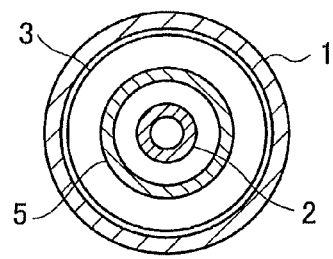
FIG. 2 is a cross-sectional view taken along the section line II-II in FIG. 1.

The bag member 3 is contained in the sheath 1, as shown in FIGS. 1 and 2.

The bag member 3 is detachable from the infusion tube 2. When the bag member 3 is detached from the infusion tube 2, the opening in the bag member is closed, and the bag member 3 in the state of being filled with a therapeutic substance is indwelled at a predetermined position in a brain region.

The bag member 3 is porous, and functions to release the therapeutic substance filled in the bag member 3. It suffices for the bag member 3 to have a release hole or holes through which a therapeutic substance can be released in a relatively slow or sustained manner. The bag member 3 may thus be formed from a nonwoven fabric, cloth, mesh, porous film or the like.

The diameter of the release hole(s) is appropriately selected at an optimum value according to the therapeutic substance used. For example, in the case where an encapsulated therapeutic substance is used, the diameter of the release hole(s) is smaller than the size of the capsules, whereby only the therapeutic substance contained in the capsules can pass through the release hole(s), while the capsules do not pass through the release hole(s). More specifically, the diameter of the release hole(s) is preferably 0.1 to 1000 μm, more preferably 1 to 300 μm.

The therapeutic substance to be filled in the bag member 3 is not specifically restricted as to its kind insofar as it is a substance for use in treatment of the brain (brain-treating substance). Examples of the therapeutic substance include medicinal liquids, neurotrophic factors, information transmission substances, genes, and cells. More specifically, examples of the medicinal liquids include lidocaine. Examples of the information transmission substances include neurotransmitters such as dopamine, adrenaline, noradrenaline, serotonin, histamine, etc., and hormones of gastrointestinal tract such as GLP-1, GIP, etc.

In addition, the form of the therapeutic substance filled in the bag member 3 is not specifically restricted. Examples of the form of the therapeutic substance include capsule, suspension, gel and sponge. From the viewpoint of sustained release, capsule and gel forms are preferred.

The opening of the bag member 3 includes a pair of plate-shaped elastic members 4 opposed to each other in connection. That is, the plate-shaped elastic members 4 are connected to the bag member 3. The plate-shaped elastic members 4 are so disposed as to make contact with the outer circumferential surface of the infusion tube 2.

The plate-shaped elastic members 4 are an example of closing means for closing the open end of the bag member 3 and tend to close the opening of the bag member 3 by their own elastic force when the bag member 3 is detached from the distal end of the infusion tube 2.

Figure 3A:
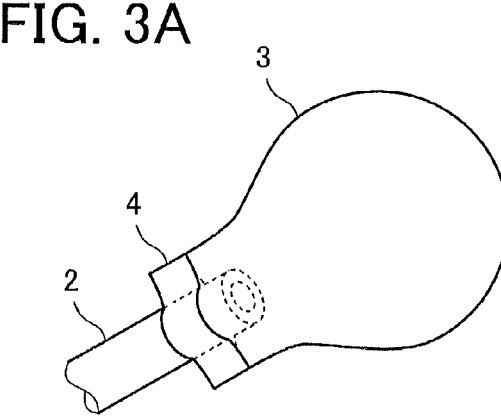

More preferably, first, as shown in FIG. 3A, when the bag member 3 is held on the distal end of the infusion tube 2, the plate-shaped elastic members 4 are elastically deformed so that central portions of the pair of plate-shaped elastic members 4 are spaced away from each other, and the infusion tube is inserted between the plate-shaped elastic members 4. Here, the plate-shaped elastic members 4 are forcibly curved along a substantially arcuate shape, and have such elasticity as to tend to return to a flat surface shape. Therefore, the pair of plate-shaped elastic members 4 press the infusion tube 2 in the manner of clamping the infusion tube 2 between them, and the bag member 3 is held onto the distal end of the infusion tube 2 by the pressing forces.

Figure 3B:
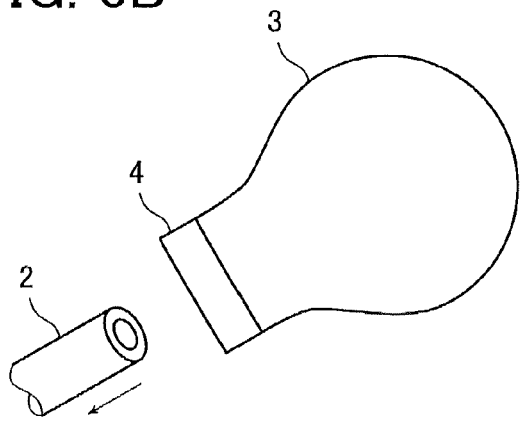

Next, when the bag member 3 is detached from the distal end of the infusion tube 2, as shown in FIG. 3B, the plate-shaped elastic members 4 are joined together or moved towards one another, whereby the opening of the bag member 3 is automatically closed. Here, the plate-shaped elastic members 4 are released from restraint by the infusion tube 2, are brought into a flat surface shape based on their own elastic force, and make contact with each other so as to fill up or close the gap between the members. As a result, the opening of the bag member 3 is automatically closed, and the therapeutic substance filling the inside of the bag member 3 can be prevented from flowing out.

While the two plate-shaped elastic members 4 are connected together at both end portions of the elastic members, the form of the connection is not specifically restricted. For example, the end portions may be joined to each other by use of an adhesive or by fusion bonding.

The medical device further has an inner tube member 5 which is inserted in the sheath 1 so as to be capable of being advanced and retracted, and which permits the infusion tube 2 to be disposed in the inside of the tube member 5. With the plate-shaped elastic members 4 pressed in the distal direction of the infusion tube 2 by use of the inner tube member 5, the plate-shaped elastic members 4 can be moved forward relative to the infusion tube 2, whereby the bag member 3 can be detached from the distal end of the infusion tube 2.

The inner tube member 5 constitutes the operating member of the medical device.

The material forming the sheath 1 is preferably a material having a certain degree of flexibility. Preferable examples of the material which can be used include thermoplastic resins such as polyolefins such as polyethylene, polypropylene, ethylene-propylene copolymer, ethylene vinyl acetate copolymer, etc., polyvinyl chloride, polyurethane, polyamides, polyamide elastomers, polyimides, silicone resins, polyether-ethyl ketone, and polyester elastomers.

As preferred examples of materials forming the infusion tube 2 and the inner tube member 5, also, the just-mentioned materials may be set forth.

Preferable examples of the material forming the bag member 3 include synthetic resins such as polypropylene, polyurethane, polyethylene, polyamides, polytetrafluoroethylene, and polyvinylidene fluoride. In addition, the material forming the bag member 3 may be a bioabsorbable material such as polylactic acid, gelatin, agarose, maltose, pectin, gellan gum, xanthan gum, alginic acid, and starch, which may be used either singly or in combination of two or more of them.

The material forming the plate-shaped elastic members 4 is preferably a material which has elasticity and a certain degree of rigidity. Examples of the material usable here include metallic materials such as stainless steel, aluminum alloys, superelastic metals, shape memory alloys, magnesium alloys, etc., and resin materials such as polyamides, polyvinyl chloride, polycarbonate, ABS, polyethylene, polypropylene, Teflon (registered trade mark), acrylic resins, polylactic acid, etc.

The operation or method of using this embodiment of the medical device will now be described below.

Figure 4A:
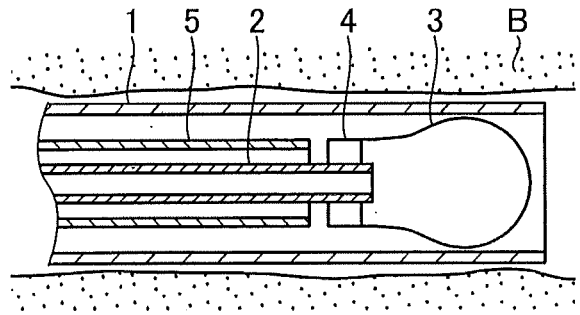

First, the medical device, in the state in which the bag member 3 is contained in the sheath 1, is inserted into a brain region B, as shown in FIG. 4A. Since neurocytes gather at surfaces of the brain tissues constituting the brain region B, the medical device is inserted while pushing aside the brain tissues.

Then, when the distal end of the sheath 1 has reached a predetermined position where treatment is needed, the insertion (forward movement) of the medical device is stopped. In this state, the therapeutic substance is filled or introduced into the bag member 3 through the infusion tube 2.

Figure 4B:
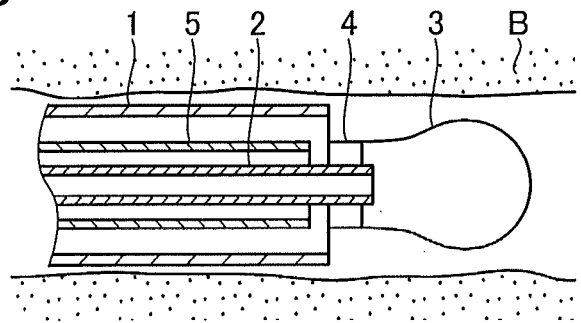

After the filling or introduction of the therapeutic substance into the bag member is completed, the sheath 1 is retracted relative to the infusion tube 2, as shown in FIG. 4B, whereby the bag member 3 held on the distal portion of the infusion tube 2 protrudes forward from the opening of the sheath 1.

It is also possible to reverse the operations shown in FIGS. 4A and 4B, whereby a process is adopted in which the sheath 1 is retracted relative to the infusion tube 2 to cause the bag member 3 held on the distal portion of the infusion tube 2 to protrude forward from the opening of the sheath 1, followed by filling the therapeutic substance into the bag member 3 through the infusion tube 2.

It is preferable to utilize the first process described above in which the bag member 3 protrudes forward from the opening of the sheath 1 after filling the therapeutic substance into the bag member 3. This is because the bag member 3 is protected by the sheath 1 at the time of filling the therapeutic substance into the bag member 3, so that the filling of the therapeutic substance can be relatively easily carried out, under little influence of the pressure exerted from the brain tissues.

Next, the inner tube member 5 is moved relative to the infusion tube 2, to detach the bag member 3 from the distal end of the infusion tube 2.

Figure 4C:
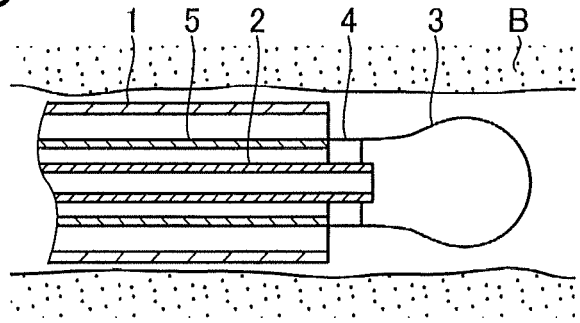
Figure 4D:
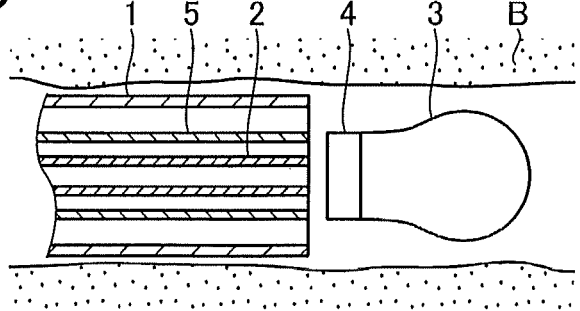

Specifically, as shown in FIG. 4C, the inner tube member 5 is moved forward (in the distal direction) relative to the infusion tube 2 so that the inner tube member 5 comes into contact with the plate-shaped elastic members 4. Subsequently, as shown in FIG. 4D, the infusion tube 2 is retracted relative to the inner tube member 5, whereby the plate-shaped elastic members 4 are moved toward the distal side of the infusion tube 2 by the inner tube member 5. As a result, the bag member 3 is detached from the distal end of the infusion tube 2, and is thus indwelled in the brain region B. In this instance, based on the elasticity of the plate-shaped elastic members 4, the opening of the bag member 3 is automatically closed, whereby the therapeutic substance filling the bag member 3 is prevented from flow out via the opening of the bag member 3.

The order of movements of the inner tube member 5 and the infusion tube 2 is not restricted to the above-described sequence. For example, an operational process may be adopted in which, starting from the condition of FIG. 4B, the inner tube member 5 is advanced relative to the infusion tube 2, to press the plate-shaped elastic members 4 until they are detached from the distal portion of the infusion tube 2, thereby detaching the bag member 3 from the distal end of the infusion tube 2.

A process may also be adopted in which, starting from the condition of FIG. 4B, the infusion tube 2 is retracted relative to the inner tube member 5, thereby detaching the bag member 3 from the distal end of the infusion tube 2.

In this way, the bag member 3 filled with the therapeutic substance can be indwelled at a desired position in the brain region B. From the bag member 3 thus indwelled, the therapeutic substance (e.g., medicinal liquids, neurotrophic factors, information transmission substances, genes, cells, etc.) is released relatively slowly or in a sustained manner. As a result, the therapeutic substance can be administered to a diseased part in the brain region B over a relatively long period of time, without any increase in the physical burden on the patient.

As described above, in the first embodiment of the medical device, the bag member 3 is filled with the therapeutic substance after the medical device is moved into the vicinity of the diseased part. Therefore, even in the case of using an encapsulated therapeutic substance or the like, collisions and friction among the capsules attendant on the movements of the medical device can be restrained.

Figure 5:
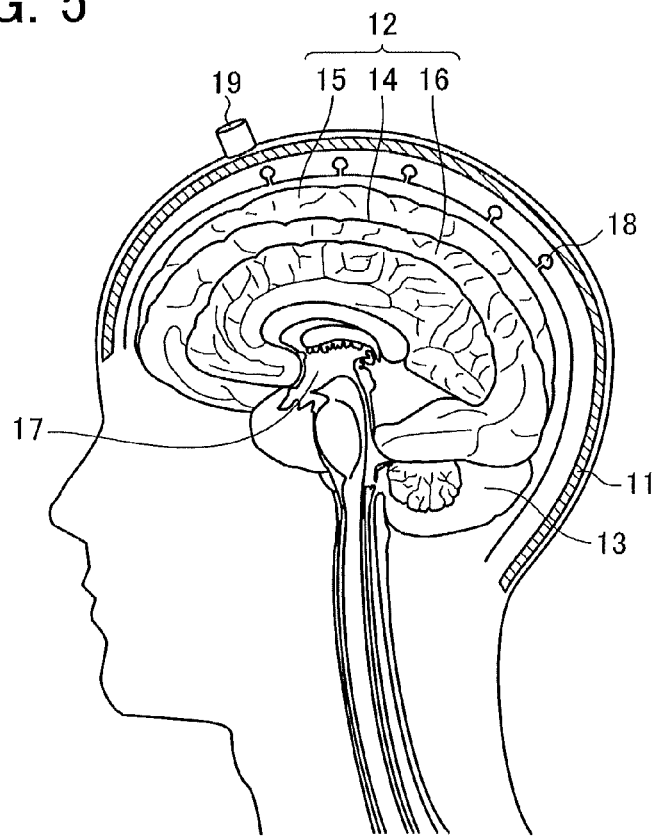
FIG. 5 is a partial cross-sectional view showing the inside of the cranial bones.

FIG. 5 illustrates the inside of the cranial bones. The brain is protected by being enveloped in a three-layer film of connective tissues, called meninx. The dura mater constituting the outermost layer is in close contact with the cranial bones 11, and the position of the brain is maintained by the dura mater. The meninx constituting the middle layer, called arachnoid, is composed of fine connective tissue fibers, and contains the cerebrospinal fluid between itself and the pia mater constituting the innermost layer. In other words, the brain is in the state of floating in the cerebrospinal fluid. The brain has the cerebrum 12 and the cerebellum 13. The cerebrum 12 is divided by the longitudinal fissure of cerebrum 14 into the right brain 15 and the left brain 16. In a bottom portion of the cranium, the cerebral ventricles including the third ventricle 17 are located. Blood vessels are abundantly present in the cerebral ventricles, and the cerebrospinal fluid is secreted from the choroid plexus in the cerebral ventricles. The cerebrospinal fluid is circulated in cavities under the arachnoid, before being absorbed into the veins from the cerebral venous sinus 18.

For example, in putting the bag member 3 indwelling in the longitudinal fissure of cerebrum 14, an aperture is first provided in the frontal region of the head, and an insertion port 19 shown in FIG. 5 is attached to the aperture. The insertion port 19 is preferably provided with a valve so that the cerebral fluid, blood and the like cannot flow to the exterior, although the medical device (e.g., the first embodiment of the medical device) can be inserted, through the insertion port 19. The medical device shown in FIG. 1 is inserted via the insertion port 19, and the distal end of the sheath 1 is located inside the longitudinal fissure of cerebrum 14.

In this condition, the above-mentioned procedure is carried out, whereby the bag member 3 can be indwelled in the longitudinal fissure 14.

As shown in FIG. 4A, in this embodiment, the bag member 3 is in a somewhat inflated shape, even before being filled with the therapeutic substance. However, the bag member 3 may be in a folded form before being filled with the therapeutic substance.

Figure 6A:
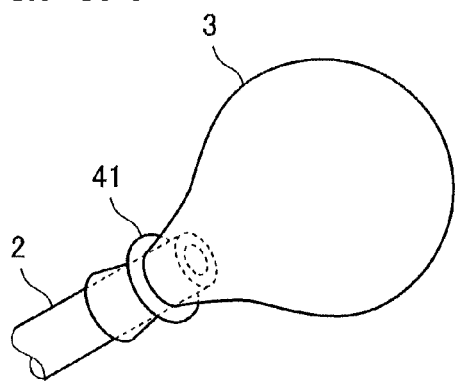
Figure 6B:
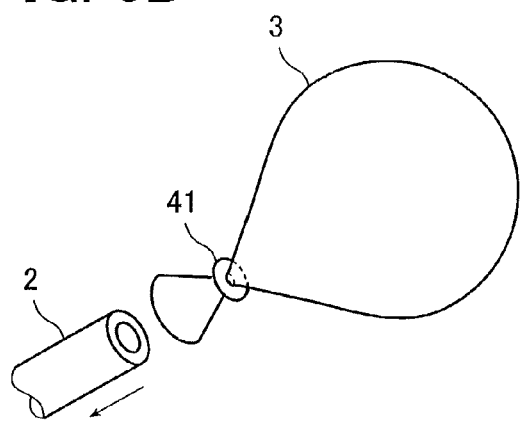

Another embodiment of the medical device is shown in FIGS. 6A and 6B. Here, another example of closing means is employed. The closing means is a ring-shaped elastic member 41 as shown in FIGS. 6A and 6B. Like the above-mentioned plate-shaped elastic members 4, the ring-shaped elastic member 14 closes the opening of the bag member 3, based on its own elastic force (elasticity).

As shown in FIG. 6A, when the bag member 3 is held on the distal end of the infusion tube 2, the ring-shaped elastic member 41 is elastically deformed to be enlarged in diameter, and the infusion tube 2 is inserted in the ring. Here, the ring-shaped elastic member 41 is forcibly enlarged in diameter, and has elasticity in the direction for decreasing in diameter. Therefore, the ring-shaped elastic member 41 presses an outer circumferential surface of the infusion tube located in the ring, through the bag member 3, and the bag member 3 is held onto the distal end of the infusion tube 2 under this pressing force.

Next, as shown in FIG. 6B, when the bag member 3 is detached from the distal end of the infusion tube 2, the bag member is released from the restraint by the infusion tube 2, and the ring-shaped elastic member 41 is reduced in diameter, based on its own elastic force. As a result, the opening in the bag member 3 is automatically closed, whereby the therapeutic substance filling the bag member 3 is prevented from flowing out.

Thus, with the ring-shaped elastic member 41 utilized, the closing means can be simplified in structure and reduced in size.

In FIGS. 6A and 6B, the ring-shaped elastic member 41 is provided outside the bag member 3. However, the ring-shaped elastic member 41 may be provided on the inside near the opening of the bag member 3, integrally with the bag member 3.

The operational use of this embodiment of the medical device shown in FIGS. 6A and 6B can be the same as the operational procedure or manner of use described above regarding the first embodiment.

Figure 7A:
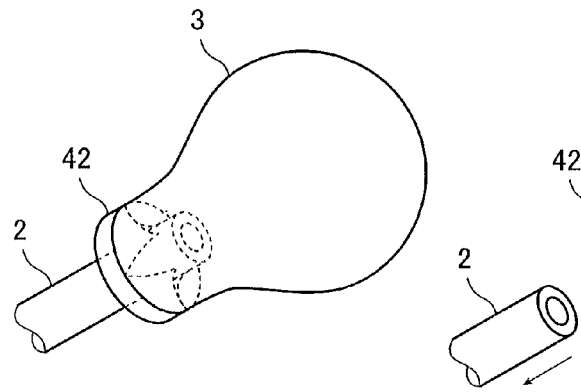
Figure 7B:
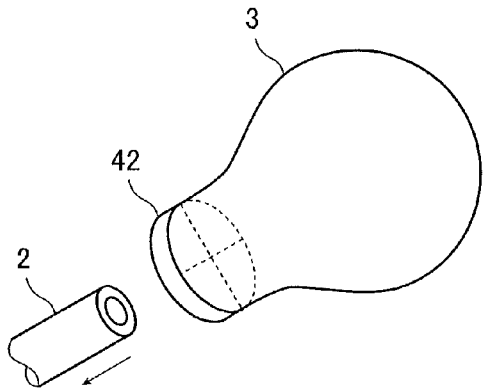

Another embodiment of the medical device is shown in FIGS. 7A and 7B. This embodiment employs another example of closing means. The closing means here is a cover member 42 provided with slit-shaped cuts and disposed in covering relation to the opening of the bag member 3. The cover member 42 tends to close the opening of the bag member 3 on the basis of its own elastic force, like the above-mentioned plate-shaped elastic members 4.

As shown in FIG. 7A, when the bag member 3 is held on the distal end of the infusion tube 2, the cover member 42 is elastically deformed so that the cuts are broadened, and the infusion tube 2 is inserted in the inside of the broadened cuts. Here, the cover member 42 is forcibly broadened, and has elasticity in the closing direction. Therefore, the cover member 42 presses an outer circumferential surface of the infusion tube disposed in the inside of the cuts, and the bag member 3 is held on the distal end of the infusion tube 2 by the pressing force.

Next, as shown in FIG. 7B, when the bag member 3 is detached from the distal end of the infusion tube 2, the cover member is released from the restraint by the infusion tube 2, and the cuts in the cover member 42 are closed on the basis of the elastic force possessed by itself. As a result, the opening of the bag member 3 is automatically closed, whereby a therapeutic substance filling the bag member 3 can be prevented from flowing out.

Thus, with the cover member 42 utilized, the closing means can be simplified in structure. In addition, after the infusion tube 2 is detached, the infusion tube 2 can be again inserted into the bag member 3 through the cover member 42.

While two straight cuts are formed in the cover member 42, the number of cuts is not particularly limited. And the slit-shaped cuts may not necessarily be in the shape of straight lines but may be in the shape of curved lines.

The operational use of the embodiment of the medical device shown in FIGS. 7A and 7B can be the same as the operational procedure or manner of use described above regarding the first embodiment.

In the above-described first, second and third embodiments, the operating member has been the inner tube member 5 having the infusion tube 2 disposed in the inside thereof. However, the medical device here is not limited to this operating member, as long as the operating member can press the closing means and can be moved forward relative to the infusion tube 2.

Figure 8:
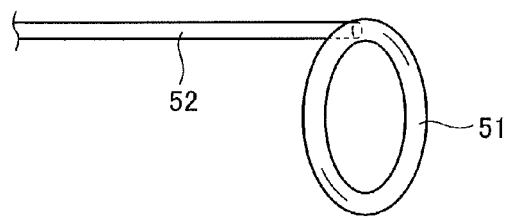
FIG. 8 is a perspective view showing a modification of an operating member.

For example, as shown in FIG. 8, the operating member may be composed of a ring-shaped section 51 making contact with the closing means, and a wire section 52 which is connected to the ring-shaped section 51 and extends in the axial direction of the sheath 1 and by which the ring-shaped section 51 can be advanced and retracted.

FIG. 9 illustrates the configuration of a distal portion of a medical device according to another embodiment. This medical device is a medical device similar to the first embodiment, except the bag member 3 (interior of the bag member) is provided with a first engaging part 60, whereas the infusion tube 2 is provided with a second engaging part 61 which extends from the distal end of the infusion tube 2. The second engaging part 61 is disengageably engaged with the first engaging part 60.

Figure 9A:
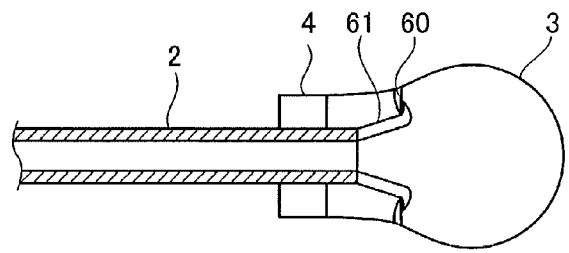

In this medical device, as shown in FIG. 9A, when the bag member 3 is held on the distal end of the infusion tube 2, the first engaging part 60 and the second engaging part 61 are engaged with each other, thereby restraining the bag member 3 from moving forward relative to the infusion tube 2. In other words, the engaging parts are restraining the bag member 3 from being positionally deviated in relation to the infusion tube 2.

Figure 9B:
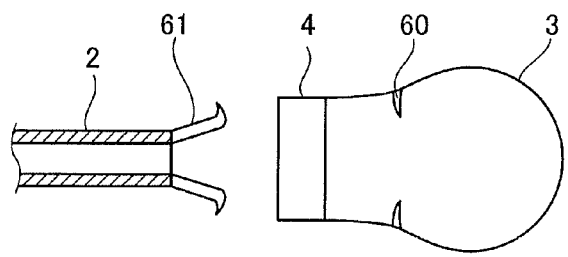

On the other hand, as shown in FIG. 9B, when the bag member 3 is detached from the infusion tube 2, a forward movement of the bag member 3 relative to the infusion tube 2 is attended by disengagement of the first engaging part 60 and the second engaging part 61 from each other.

Providing such engagement between the bag member 3 and the infusion tube 2 helps ensure that when filling a therapeutic substance into the bag member 3 through the infusion tube 2, a positional deviation in which the bag member 3 is moved forward relative to the infusion tube 2 can be restrained from being induced, for example, by the pressure of the therapeutic substance.

The first engaging part 60 is a hook-shaped projected part configured to engage the second engaging part 61.

Figure 10:
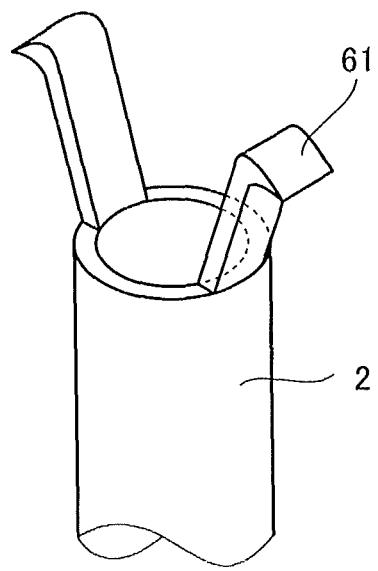
FIG. 10 is a perspective view of an infusion tube having a second engaging part.

In addition, as shown in FIG. 10, the second engaging part 61 is composed of two arms which extend in the axial direction from the distal end of the infusion tube 2 and which have their distal portions bent in a hook-like shape. The number of engaging parts and the number of arms are not limited to the number described above and illustrated in the drawings.

The shapes of the first engaging part 60 and the second engaging part 61 are not restricted to the shapes mentioned above, but can be any of various shapes suited to the method of engagement used.

The materials forming the first engaging part 60 and the second engaging part 61 are not specifically limited; from the viewpoint of ease of engagement and disengagement. However, the engaging parts are preferably formed from elastic material such as rubber.

The embodiment described above is configured so that the second engaging part 61 engages the first engaging part 60 provided inside the bag member 3. However, a configuration may be adopted in which the second engaging part 61 engage the plate-shaped elastic members 4, thereby restraining positional deviation of the bag member 3 from occurring. In other words, the plate-shaped elastic members 4 may function as the engaging part.

Figure 11:
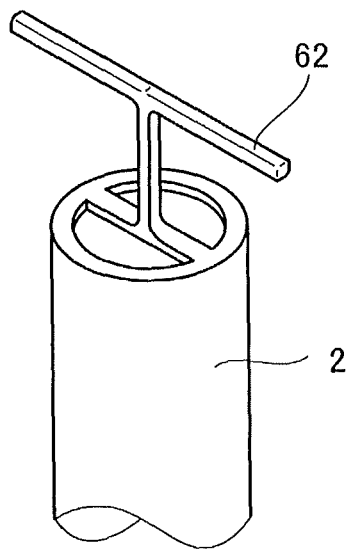
FIG. 11 is a perspective view of a modification of an infusion tube having a second engaging part.

As a modification of the second engaging part, for example, a roughly T-shaped second engaging part 62 as shown in FIG. 11 may be adopted. The second engaging part 62 is configured to include an arm section which extends in the axial direction from the distal end of the infusion tube 2, and a rod-shaped section which is connected to the distal end of the arm section and is so attached as to engage the first engaging part 60 in a bridging manner.

Figure 12A:
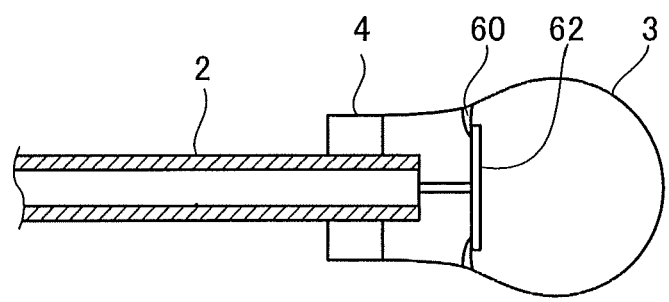

In this case, as shown in FIG. 12A, when the bag member 3 is held on the distal end of the infusion tube 2, the rod-shaped section of the second engaging part 62 is so disposed as to engage the first engaging part 60 in a bridging manner, whereby the bag member 3 is restrained from moving forward relative to the infusion tube 2.

Figure 12B:
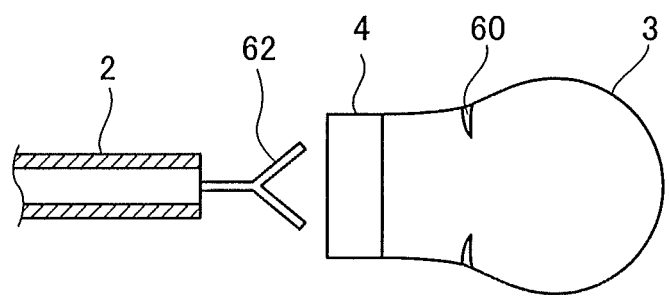

On the other hand, as shown in FIG. 12B, when the bag member 3 is detached from the infusion tube 2, it is ensured that when the bag member 3 is moved forward relative to the infusion tube 2, the rod-shaped section of the second engaging part 62 is bent, whereby the first engaging part 60 and the second engaging part 62 are disengaged from each other.

The detailed description above describes various embodiments of a medical device and operational method involving use of the medical device. But it is to be understood that the invention is not limited to those precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device comprising:
a sheath possessing an open distal end;
an infusion tube positioned inside the sheath and movable in an advancing and retracting manner relative to the sheath, the infusion tube possessing an interior which opens at a distal end of the infusion tube;
a porous bag member including an opening which opens into an interior of the bag member, the porous bag member being detachably positioned at the distal end of the infusion tube, with the interior of the porous bag member communicating with the interior of the infusion tube, the bag member being positioned in the sheath;
closing means disposed at the opening of the bag member for closing the opening of the bag member by elastic force when the bag member is detached from the distal end of the infusion tube;
an operating member positioned in the sheath and movable in an advancing and retracting manner relative to the infusion tube to detach the bag member from the distal end of the infusion tube by moving the closing means forward relative to the infusion tube;
the bag member being configured to be indwelled in a brain region by a process comprising:
inserting the sheath into the brain region, filling the bag member with a therapeutic substance by way of the infusion tube, and retracting the sheath relative to the infusion tube until the bag member protrudes forward from the distal end of the sheath, with the inserting, filling and retracting being performed in any order; and
thereafter moving the operating member relative to the infusion tube to detach the bag member from the distal end of the infusion tube.

2. The medical device according to claim 1, wherein:
the closing means comprises a pair of plate-shaped elastic members opposed to each other; and
the pair of plate-shaped elastic members being elastically deformed so as to be spaced from each other with the infusion tube positioned between the plate-shaped elastic members to hold the bag member on the distal end of the infusion tube, the plate-shaped elastic members being joined to each other so that the opening of the bag member is automatically closed when the bag member is detached from the distal end of the infusion tube.

3. The medical device according to claim 1, wherein:
the closing means comprises a ring-shaped elastic member; and
the bag member is held on the distal end of the infusion tube by the ring-shaped elastic member which encircles the distal end of the infusion tube and is elastically deformed so as to be enlarged in diameter, and detaching the bag member from the distal end of the infusion tube causes the ring-shaped elastic member to be reduced in diameter to automatically close the opening of the bag member.

4. The medical device according to claim 1, wherein:
the closing means comprises a cover member disposed across and covering the opening of the bag member, the cover member including a slit-shaped cut; and
the bag member is held on the distal end of the infusion tube by the cover member being elastically deformed to enlarge the cut of the cover member and the infusion tube being positioned in the cut, and detaching the bag member from the distal end of the infusion tube causes the infusion tube to move out of the cut to close the cut and automatically close the opening of the bag member.

5. The medical device according to claim 1, wherein the operating member is an inner tube member, and the infusion tube is disposed inside the inner tube member.

6. The medical device according to claim 1, wherein:
the interior of the bag member includes a first engaging part;
the infusion tube includes a second engaging part for disengageable engaging the first engaging part, the second engaging part extending from a distal portion of the infusion tube; and
the bag member being detachably positioned at the distal end of the infusion tube by the first engaging part and the second engaging part engaging each other to restrain the bag member from being positionally deviated relative to the infusion tube, the first engaging part and the second engaging part being disengaged from each other to detach the bag member from the distal end of the infusion tube.

7. The medical device according to claim 2, wherein the operating member is an inner tube member, and the infusion tube is positioned in the inner tube member.

8. The medical device according to claim 3, wherein the operating member is an inner tube member, and the infusion tube is positioned in the inner tube member.

9. The medical device according to claim 4, wherein the operating member is an inner tube member, and the infusion tube is positioned in the inner tube member.

10. The medical device according to claim 2,
the interior of the bag member includes a first engaging part;
the infusion tube includes a second engaging part for disengageable engaging the first engaging part, the second engaging part extending from a distal portion of the infusion tube; and
the bag member being detachably positioned at the distal end of the infusion tube by the first engaging part and the second engaging part engaging each other to restrain the bag member from being positionally deviated relative to the infusion tube, the first engaging part and the second engaging part being disengaged from each other to detach the bag member from the distal end of the infusion tube.

11. The medical device according to claim 3, the interior of the bag member includes a first engaging part;
the infusion tube includes a second engaging part for disengageable engaging the first engaging part, the second engaging part extending from a distal portion of the infusion tube; and
the bag member being detachably positioned at the distal end of the infusion tube by the first engaging part and the second engaging part engaging each other to restrain the bag member from being positionally deviated relative to the infusion tube, the first engaging part and the second engaging part being disengaged from each other to detach the bag member from the distal end of the infusion tube.

12. The medical device according to claim 4, the interior of the bag member includes a first engaging part;

the infusion tube includes a second engaging part for disengageable engaging the first engaging part, the second engaging part extending from a distal portion of the infusion tube; and the bag member being detachably positioned at the distal end of the infusion tube by the first engaging part and the second engaging part engaging each other to restrain the bag member from being positionally deviated relative to the infusion tube, the first engaging part and the second engaging part being disengaged from each other to detach the bag member from the distal end of the infusion tube.

13. The medical device according to claim 5, the interior of the bag member includes a first engaging part;

the infusion tube includes a second engaging part for disengageable engaging the first engaging part, the second engaging part extending from a distal portion of the infusion tube; and the bag member being detachably positioned at the distal end of the infusion tube by the first engaging part and the second engaging part engaging each other to restrain the bag member from being positionally deviated relative to the infusion tube, the first engaging part and the second engaging part being disengaged from each other to detach the bag member from the distal end of the infusion tube.

14. A method for delivering a therapeutic substance to a brain region comprising:

moving an infusion tube toward the brain region to position a bag member, which is detachably mounted at a distal end of the infusion tube, at the brain region, the bag member possessing an open end which opens into an interior of the bag member, the infusion tube being positioned in the opening while a portion of the bag member surrounds the distal end of the infusion tube, the infusion tube being movably positioned inside an inner tube member so that the inner tube member is movable relative to the infusion tube and the bag member;

moving the inner tube member in an advancing direction relative to the infusion tube and the bag member to push the bag member off the distal end of the infusion tube and position the bag member at the brain region;

automatically closing the open end of the bag member when the bag member is pushed off the distal end of the infusion tube; and delivering a therapeutic substance in the bag member to the brain region.

15. The method according to claim 14, wherein the bag member is made of a porous material and the therapeutic substance in the bag member is delivered to the brain region by passing through the porous material.

16. The method according to claim 14, wherein the infusion tube includes a hollow interior communicating with an opening at the distal end of the infusion tube, and further comprising introducing the therapeutic substance into the bag member by way of the hollow interior in the infusion tube and the opening at the distal end of the infusion tube.

17. The method according to claim 14, wherein the therapeutic substance is introduced into the bag member after the bag member is positioned at the brain region.

18. The method according to claim 14, wherein the infusion tube, the bag member and the inner tube are positioned inside a sheath, and the infusion tube is moved toward the brain region to position the bag member at the brain region by moving the sheath, together with the infusion tube, the bag member and the inner tube member, towards the brain region, followed by retracting the sheath relative to the inner tube member, the infusion tube and the bag member, to expose the bag member which is positioned distally of a distal end of the inner tube member.

19. The method according to claim 18, wherein the infusion tube includes a hollow interior communicating with an opening at the distal end of the infusion tube, and further comprising introducing the therapeutic substance into the bag member by way of the hollow interior in the infusion tube and the opening at the distal end of the infusion tube, the therapeutic substance being introduced into the bag member before the sheath is retracted relative to the inner tube member, the infusion tube and the bag member, to expose the bag member.

20. The method according to claim 18, wherein the infusion tube includes a hollow interior communicating with an opening at the distal end of the infusion tube, and further comprising introducing the therapeutic substance into the bag member by way of the hollow interior in the infusion tube and the opening at the distal end of the infusion tube, the therapeutic substance being introduced into the bag member after the sheath is retracted relative to the inner tube member, the infusion tube and the bag member, to expose the bag member.

* * * * *